United States Patent
Nouaille et al.

(10) Patent No.: US 9,650,469 B2
(45) Date of Patent: May 16, 2017

(54) PROCESS OR PRODUCING POLYHYDROXYALKANOATES FROM PRECURSORS OBTAINED BY ANAEROBIC FERMENTATION FROM FERMENTABLE BIOMASS

(71) Applicant: AFYREN, Saint Beauzire (FR)

(72) Inventors: Régis Nouaille, Cournon D'Auvergne (FR); Jérémy Pessiot, La Charite sur Loire (FR); Marie Thieulin, Saint Andre les Vergers (FR)

(73) Assignee: AFYREN, Saint Beauzire (FR)

( * ) Notice: Subject to any disclaimer, the term of this patent is extended or adjusted under 35 U.S.C. 154(b) by 0 days.

(21) Appl. No.: 15/053,666

(22) Filed: Feb. 25, 2016

(65) Prior Publication Data

US 2016/0251474 A1 Sep. 1, 2016

(30) Foreign Application Priority Data

Feb. 27, 2015 (FR) ...................... 15 51672

(51) Int. Cl.
| | |
|---|---|
| C08G 64/00 | (2006.01) |
| C08G 63/06 | (2006.01) |
| C08G 63/78 | (2006.01) |
| C07C 51/363 | (2006.01) |
| C07C 51/367 | (2006.01) |
| C12P 7/40 | (2006.01) |
| C12P 7/42 | (2006.01) |
| C12P 7/62 | (2006.01) |
| C08G 63/02 | (2006.01) |

(52) U.S. Cl.
CPC ............ *C08G 63/06* (2013.01); *C07C 51/363* (2013.01); *C07C 51/367* (2013.01); *C08G 63/78* (2013.01); *C12P 7/40* (2013.01); *C12P 7/42* (2013.01); *C12P 7/625* (2013.01)

(58) Field of Classification Search
CPC ...................................... C08G 63/06
USPC ........................ 528/271, 272, 274
See application file for complete search history.

(56) References Cited

U.S. PATENT DOCUMENTS

| | | |
|---|---|---|
| 3,642,887 A | 2/1972 | Jackisch |
| 4,377,638 A | 3/1983 | Bryant et al. |
| 5,686,275 A | 11/1997 | Casey et al. |
| 2011/0159556 A1* | 6/2011 | Pieja ........ C12P 7/625 435/135 |

FOREIGN PATENT DOCUMENTS

| | | |
|---|---|---|
| CN | 102030669 | 4/2011 |
| DE | 2810975 | 9/1979 |
| EP | 0110761 | 6/1984 |
| EP | 0295550 | 8/1988 |
| EP | 2749650 | 2/2014 |
| WO | 03/062439 | 7/2003 |
| WO | 03062439 | 7/2003 |
| WO | 2013/022998 | 2/2013 |
| WO | 2013022998 | 2/2013 |
| WO | 2014/170603 | 10/2014 |
| WO | 2014170603 | 10/2014 |
| WO | 2016135396 | 9/2016 |
| WO | 2016135397 | 9/2016 |

OTHER PUBLICATIONS

French Search Report in corresponding French Application No. 1551672, dated Dec. 15, 2015.
Guillermo Colon et al., On-line Removal of Volatile Fatty Acids From Celss Anaerobic Bioreactor VIA Nanofiltration, Life Support & Biosphere Science, vol. 7, pp. 291-299.
French Search Report for FR 1551672 dated Dec. 15, 2015.
Colon, G et al, "On-Line removal of volatile fatty acids from CELISS anaerobic bioreactor via nanofiltration", Life Support & Biosphere Science: International journal of Earth Space, COgnizant Communication Corp, Elmsford, Ny, USA, vol. 7, No. 4, Jan. 1, 2001.
Sisler H. H. and Cheronis N.D., "Studies in Ammonolysis. II. Ammonolysis of [alpha]-Halogen Acids in Liquid Ammonia 1", The journal of organic Chemistry, vol. 06, No. 4, Jul. 1, 1941 (Jul. 1, 1941), pp. 467-478.
Perkin, W.H., "Ueber die Einwirkung des Broms auf Essigsqure", Justus Liebigs Annalen Der Chemie, vol. 108, No. 1, Jan. 1, 1858 (Jan. 1, 1858), pp. 106-113.

* cited by examiner

*Primary Examiner* — Terressa Boykin

(57) ABSTRACT

The process for producing polyhydroxyalkanoates or PHA from volatile fatty acid (VFA) molecules, referred to as precursors, produced by anaerobic fermentation from fermentable biomass, characterized in that it comprises at least the following steps:
a) extracting the volatile fatty acid (VFA) molecules, without stopping the fermentation, via an extraction means chosen from means that are, at least, insoluble in the fermentation medium,
b) collecting, outside the fermentation reactor, the volatile fatty acid (VFA) molecules once they have been extracted,
c) synthesizing, by halogenation, using a type of volatile fatty acid (VFA) chosen from the volatile fatty acids collected in step b) and defined according to the desired type of PHA, a given α-halo acid,
d) synthesizing from this α-halo acid molecules of a given α-hydroxy acid by reaction with a base,
e) polymerizing using the α-hydroxy acid obtained a defined polyhydroxyalkanoate (PHA).

10 Claims, No Drawings

PROCESS OR PRODUCING POLYHYDROXYALKANOATES FROM PRECURSORS OBTAINED BY ANAEROBIC FERMENTATION FROM FERMENTABLE BIOMASS

The present invention relates to a process for producing polyhydroxyalkanoates from precursors obtained by anaerobic fermentation from fermentable biomass.

Hereinbelow, to facilitate the reading, the polyhydroxyalkanoates will be referred to by their abbreviation: PHA. This family comprises several molecules, as a function of the number of carbons.

PHA are thermoplastic polyesters that may be produced by microbial fermentation from sugars of plant origin, in particular corn starch or waste vegetable matter. Microorganisms produce PHA when conditions of deficiency in certain metabolites associated with an excess offer of carbon are encountered. In other words, the microorganisms then accumulate carbon, originating from sugars, in the form of PHA granules. PHAs are used, for example, as constituent material of packagings or in the medical field as suture material. They substitute for petroleum-based polymers.

Fermentation processes are known using pure selected strains of microorganisms and also a specific substrate for producing PHAs. Such a solution is difficult to exploit at an industrial scale for an acceptable production cost.

A process adapted to industrial use is also known from EP-A-2 749 650. The substrate used is derived from effluents and enriched in the volatile fatty acids (VFA), which are known to be PHA precursors. By using a bacterial consortium and by alternating phases of growth of the biomass and phases of deficiency, in a controlled manner, the bacterial growth and the production of PHA are stimulated. However, such a process involves precise control of the fermentation conditions and a suitable treatment for extracting the PHAs produced, which involves a relatively heavy installation. Moreover, such extraction cannot be performed continuously and it does not allow a production of all types of PHA. Another drawback of this process is its specificity: it can only produce microbial PHAs, i.e. PHAs produced by microorganisms.

The invention is more particularly directed toward overcoming these drawbacks by proposing a process for producing PHA that makes it possible to produce various types of PHA, especially non-protein-generating amino acids, easily and without the constraints associated with the known production methods of the prior art.

To this end, one subject of the invention is a process for producing polyhydroxyalkanoates or PHA from volatile fatty acid (VFA) molecules, referred to as precursors, produced by anaerobic fermentation from fermentable biomass, characterized in that it comprises at least the following steps:
a) extracting the volatile fatty acid (VFA) molecules, without stopping the fermentation, via an extraction means chosen from means that are, at least, insoluble in the fermentation medium,
b) collecting, outside the fermentation reactor, the volatile fatty acid (VFA) molecules once they have been extracted,
c) synthesizing, by halogenation, using a type of volatile fatty acid (VFA) chosen from the volatile fatty acids collected in step b) and defined according to the desired type of PHA, a given α-halo acid,
d) synthesizing from this α-halo acid molecules of a given α-hydroxy acid by reaction with a base,
e) polymerizing using the α-hydroxy acid obtained a defined polyhydroxyalkanoate (PHA).

Thus, such a process makes it possible to combine a phase for the continuous production of precursors via microorganisms with a synthesis phase performed outside fermentation, which allows easy control of the various parameters, while at the same time allowing greater variability in the type of polyhydroxyalkanoates (PHA) produced.

Such a process makes it possible continuously to provide precursors, i.e. volatile fatty acids, while at the same time preserving the production capacity of the microorganisms present in the bioreactor.

Specifically, the extraction and collection steps a) and b) make it possible not only to extract and to collect continuously the volatile fatty acid molecules produced in the fermentation reactor, but also to preserve the microorganisms responsible for this production. Specifically, the extraction, and de facto the collection, is performed under conditions that are at least non-lethal for all of the microorganisms, i.e. under biocompatible extraction and collection conditions, since the extraction preserves the activity of the microorganisms and the collection is performed outside the fermentation reactor.

In this way, the problems associated with the accumulation of metabolites in the fermentation reactor are overcome, for example the acidification of the fermentation medium by accumulation of the volatile fatty acids produced, which are harmful to the microorganisms. The amount and activity of the microorganisms are maintained at a higher-level, close to the initial level, throughout the fermentation cycle.

By providing a continuous and regular production of VFA, this offers a readily and rapidly usable source of varied precursors. In the process that is the subject of the invention, this use takes place, via step c), by chemical synthesis and thus under readily controllable and modifiable conditions, this also offering greater variability in the type of molecules synthesized. Specifically, during step c), depending on the VFA selected to perform the halogenation, a given type of α-halo acid is obtained and thus, thereafter, a defined type of α-hydroxy acids is obtained and thus a given type of α-PHA is obtained. The invention also makes it possible to combine several α-hydroxy acids thus obtained to produce, during the final step of the process, heteropolymers.

Several types of PHA exist which are of interest for an industrial, cosmetic, medical, food or other use. Examples that may be mentioned include polyhydroxybutyrate or PHB and poly(3-hydroxybutyrate-co-3-hydroxyvalerate) or PHBV. Mention may also be made, among the types of PHA, of the production of polyglycolic acid or PGA or of polylactic acid or PLA, given that, via the known process of the prior art, it is not possible to produce PLA directly, the latter must be polymerized from a production by fermentation of lactic acid.

In other words, by means of the invention, the synthesis of several types of PHA, namely homo-, co- or heteropolymer types, may be performed, in a regular and controlled manner, from a biosourced substrate by combining a biological production with a chemical production.

Such a process makes it possible, during the anaerobic fermentation phase, to use fermentable biomass. The term "fermentable biomass" denotes herein an organic substrate, which is advantageously not food-grade, obtained from waste, byproducts and coproducts formed from organic material, i.e. from biomass, derived from human activities, whether they be domestic, industrial, agricultural, forestry, aquatic, agro-industrial, derived from animal husbandry or the like. Nonlimiting examples of organic substrates that may be mentioned include manures, the organic fraction of domestic refuse, abattoir coproducts, cellulose or lignocellulose-based residues originating from the agro-industry, such as those derived from the transformation of sugar cane (bagasse), sunflower or soybean.

The term "anaerobic fermentation" means fermentation performed under anaerobic conditions by eukaryotic or prokaryotic microorganisms, such as bacteria, fungi, algae or yeasts.

According to advantageous but not obligatory aspects of the invention, such a process may comprise one or more of the following characteristics:

during step c), the halo compound used is dibromine.
During step c), the halo compound used is other than dibromine.
During step c), acetic anhydride is used in a molar percentage relative to the volatile fatty acid in the region of 12%.
During step c), an anhydride corresponding to the volatile fatty acid (VFA) to be halogenated is used.
During step c), the temperature at which the bromination reaction is performed is from 20° C. to 40° C. below the boiling point of the volatile fatty acid.
During step d), the base used is sodium hydroxide.
During step d), the sodium hydroxide is in equimolar amount with the α-halo acid.
During step d), the reaction of the α-halo acid with sodium hydroxide is performed between 20° C. and 120° C., advantageously between 50° C. and 90° C.
During step d), the reaction of the α-halo acid with sodium hydroxide is optimal for a temperature in the region of 50° C. if the α-halo acid contains at least four carbons and for a temperature in the region of 90° C. if the α-halo acid contains less than four carbons.

The invention will be understood more clearly and other advantages thereof will emerge more clearly on reading the description of several embodiments of the invention, which is given by way of nonlimiting example.

The various steps of the process are now described with reference to several embodiments, it being understood that the steps that are known per se are not detailed.

First, the substrate used is advantageously not treated, i.e. it has not undergone any physicochemical or enzymatic pretreatment. This substrate is predominantly constituted of fermentable biomass. As additional nonlimiting examples, mention may be made of agricultural or plant-based waste (straw, bagasse, corn distillation residues, grass, wood, mowings), paper-based waste (cardboard, paper), agrifood waste, abattoir waste, the organic fraction of domestic refuse, animal husbandry effluents (manures, slurries, droppings), algae, aquaculture waste, forestry activity waste or fermentable coproducts from the cosmetics industry. Certain substrates contain organic molecules, such as organic acids, which will have little or no influence on the fermentation process. On the other hand, these molecules may be found in the fermentation medium and may participate, for example, in the production of the defined final organic molecules.

As a reminder and in a known manner, the substrate is introduced into a fermentation reactor, which is known per se and dimensioned for the desired production, whether this production be at the laboratory scale to perform tests or at the industrial scale in the case of a production. In other words, the fermentation reactor or bioreactor has a volume ranging from a few liters to several hundred cubic meters, depending on the need.

Microorganisms are advantageously initially introduced into the fermentation reactor, in an amount sufficient to start the fermentation. The microorganisms are advantageously inoculated in the form of a consortium. The term "consortium" denotes a mixture or mix of eukaryotic and prokaryotic microorganisms, whether they be bacteria, yeasts, fungi or algae. These various microorganisms originate essentially from natural ecosystems, advantageously, but not exclusively, from anaerobic ecosystems such as, as nonlimiting examples, the anaerobic zone of aquatic media such as the anoxic zone of certain lakes, soils, marshes, purification sludges, the rumen of ruminants or the intestine of termites. It should be borne in mind that the qualitative and quantitative distribution of the various types and species of microorganisms in the consortium is not precisely known and above all may vary within wide proportions. It turns out that this qualitative and quantitative diversity surprisingly affords robustness and adaptability of the microorganisms, which make it possible to ensure optimum use of the substrates, irrespective of the composition of these substrates and under variable fermentation conditions.

Moreover, due to the fact that the substrate is used in unmodified form, i.e. it is not sterilized or, more generally, it is not freed of the microorganisms it contains prior to its introduction into the bioreactor, it turns out that the microorganisms endemic to the substrate are, de facto, incorporated into the consortium or at least combined therewith in the bioreactor.

Moreover, the fermentation takes place under anaerobic conditions, more precisely when the redox potential is less than −300 mV, advantageously between −550 mV and −400 mV and when the pH is less than 8, preferably between 4 and 7. The fermentation is advantageously limited to the production of "precursor" fermentation metabolites, namely volatile fatty acids or VFA containing from two to eight carbons, preferentially from two to six. A reaction similar to the phenomenon of acidosis encountered in ruminants is thus induced while at the same time having a methane production close to zero. Methane is, generally, one of the final fermentation metabolites obtained during anaerobic fermentation by microorganisms derived from natural ecosystems.

The fermentation leads, in a first stage, to the formation of volatile fatty acids mainly containing from two to four carbons, for instance acetic acid, propionic acid and butyric acid. Long-chain volatile fatty acids, thus longer than four carbons, such as valeric acid, caproic acid, heptanoic acid or octanoic acid, are also obtained, in smaller amount. By continuing the fermentation and/or by increasing the amount of microorganisms in the bioreactor, if need be with selected microorganisms, it is possible to promote the production of long-carbon-chain VFA, thus longer than four carbons.

In other words, the volatile fatty acids produced in amount during the fermentation are essentially volatile fatty acids of two to six carbons.

The fermentation is, in all cases, conducted to ensure the production of VFA, in the liquid phase. Typically, the fermentation time is between 1 and 7 days, preferentially between 2 and 4 days. The concentration of metabolites obtained in the fermentation medium on conclusion of this period is variable, but, for volatile fatty acids, is generally from about 10 to 20 g/L, depending on the volatile fatty acids, it being understood that under certain conditions, it may be greater than 35 g/L, for example in the region of 50 g/L. At the end of the fermentation step, the fermentation medium is at an acidic pH, which is generally between 4 and 6, due to the presence of the volatile fatty acids in the fermentation medium.

When the production of VFA reaches a defined amount, generally in the permanent regime phase of the fermentation, step a) of extraction of the molecules is initiated. Preferably, but not mandatorily, this defined amount of VFA corresponds to a slowing-down of the growth of the microorganisms, thus in the region of an inhibition threshold for the microorganisms.

The extraction means is chosen from liquid or solid extraction means, which are, at least, insoluble in the fermentation medium. When the extraction means is liquid, thus when it is a solvent, preferentially, the density of the solvent is less than that of the fermentation medium.

More precisely, the extraction is performed with a solid or liquid extraction means, the operating conditions of which make it possible to preserve the activity and/or growth of the microorganisms under the fermentation conditions prevailing in the bioreactor and which are defined to perform the fermentation. The VFA molecules are preferentially extracted by molecular families and then advantageously separated individually via techniques that are known per se.

When molecules such as volatile fatty acids are extracted from the fermentation medium, de facto the acidification of the fermentation medium by these acids is reduced. Thus, the fermentation, and thus the production of metabolites, continues under conditions similar to the initial conditions, the fermentation medium remaining sparingly acidic.

The extraction is advantageously performed continuously or at least sequentially, for example with an extraction every 12 hours. In other words, it is possible to continue the fermentation while extracting the metabolites produced, either gradually as they are produced or regularly.

Liquid-liquid extraction with organic solvents as an extraction means is the extraction method preferentially, but not exclusively, adopted.

In one embodiment, the extraction is not performed in a member separate from the fermentation reactor, but directly in said reactor. The solvent is introduced, for example, via a device of bubbler type located at the bottom of the reactor. As a variant, an extraction member is coupled with the reactor, a communication with the fermentation medium being arranged.

On conclusion of the extraction, the collection step b) is performed. During this step, the VFAs are collected from the organic phase via techniques that are known per se, such as distillation or evaporation.

The collection is performed either as a mixture of VFAs or by type of VFA. It is clear that the choice of VFA or of the mixture of VFAs is determined by the type of final molecule(s) desired. For this, the collection conditions, typically the evaporation or distillation parameters, are adapted.

Once this collection step has been performed, the following step c) is performed. This is advantageously, but not exclusively, performed after the collection step. As a variant, it is performed at another moment and/or another place, the VFAs produced being transported and/or stored, according to techniques that are known per se.

This halogenation step consists in reacting a halogen with a VFA so as to produce an α-halo acid, which is a highly reactive type of molecule and thus particularly advantageous for producing other molecules. Such a reaction, which is known per se, is performed by adding bromine, which is preferred, it being understood that the other halogens may be used, namely chlorine, fluorine or iodine or halogenated molecules such as phosphorus trihalides, halo acids or acyl halides.

Dibromine was selected since a brominated α-halo acid is more reactive than the corresponding chlorinated α-halo acid, a carbon-bromine bond being easier to break than a carbon-chlorine bond. Furthermore, dibromine is easier to handle due to its liquid form.

To perform the α-bromo acid synthesis, the route using an anhydride, in this instance acetic anhydride, and pyridine was adopted. It is clear that other synthetic routes, for example with polyphosphoric acid or phosphorus trihalides, are known per se. Tests with polyphosphoric acid were conducted, but the results were inconclusive, inter alia due to the high viscosity of this compound which makes it difficult to handle.

Chlorination tests were also conducted by the Applicant for the synthesis of α-chloro acids, for example with trichloroisocyanuric acid. The results obtained are inferior, in terms of yield and of ease of implementation, to those obtained with dibromine.

The synthetic route using an anhydride corresponding to the volatile fatty acid that it is desired to halogenate is advantageous and makes it possible to obtain an α-halo acid, in this instance an α-bromo acid of a given type. The use of acetic anhydride with other VFAs and/or with a mixture of VFAs of two to six carbons makes it possible to obtain a mixture of α-halo acids of two to six carbons.

Tests using acetic acid (VFA containing two carbons), propionic acid (VFA containing three carbons), butyric acid (VFA containing four carbons), caproic acid (VFA containing six carbons) and also a mixture of VFAs of two to six carbons were performed by varying the amount of acetic anhydride and also other parameters such as the temperature.

During the various tests, a protocol is respected. It involves, in a preliminary phase, heating to reflux an initial mixture of VFA, of acetic anhydride and of pyridine. Next, during the actual bromination, dibromine is added slowly, over several hours, at a temperature below the boiling point of the mixture, and, once the dibromine has been added, the mixture is again brought to reflux before being cooled. At the end of the reaction, advantageously, water is added to destroy the anhydride present. The α-bromo acid is then extracted via various methods, depending on the acid. These are, for example, distillation or separative extraction.

The initial temperature, for bringing the mixture to reflux, is between 120° C., for VFAs containing two carbons, and 200° C., for VFAs containing six carbons. The bromination temperature ranges from 80° C. to 180° C., depending on whether the VFAs contain from two to six carbons. The bromination reaction time, and thus de facto the dibromine addition time, varies from about one hour for VFAs containing six carbons to about four hours for VFAs containing two carbons.

Tests of bromination of volatile fatty acids containing two, three, four or six carbons were performed, along with a test on a mixture of volatile fatty acids:
  acetic acid (C2): 0.53 mol
  propionic acid (C3): 0.53 mol
  butyric acid (C4): 0.53 mol
  caproic acid (C6): 0.24 mol
  mixture of VFAs from C2 to C6: 0.54 mol.

The amount of dibromine added is 0.21 mol or 0.11 mol such that the volatile fatty acid is in excess. Advantageously, the Applicant has found that a mole ratio of 2:1 in favor of the VFA is optimal.

The amount of anhydride added is, for each acid, 0.06 mol for one test and 0.03 mol for another test.

The VFA mixture comprises acetic acid (C2), propionic acid (C3), butyric acid (C4), valeric acid (C5) and caproic acid (C6).

The reflux temperatures, during the preliminary phase, vary according to the VFA: 120° C. for acetic acid; 120° C. and 140° C. for the tests with propionic acid; 150° C. and 160° C. for butyric acid; 200° C. for caproic acid and 180° C. for the mixture.

The bromination temperatures for the various tests with each acid are from 10° C. to 50° C. and advantageously from 20° C. to 40° C. below the reflux temperatures and thus the boiling point of the volatile fatty acid.

The yields and purities of the α-bromo acids obtained on conclusion of the various tests are collated below in Table 1. The VFAs are denoted, for simplicity, by the number of carbons.

TABLE 1

| Acids | Amount of anhydride (mol) | Bromination time (h) | Reflux temperature (° C.) | Bromination temperature (° C.) | Yield (%) | Purity (%) |
|---|---|---|---|---|---|---|
| C2 | 0.06 | 2.2 | 120 | 100 | 87 | 98 |
| C2 | 0.03 | 4 | 120 | 90 | 80 | 93 |
| C3 | 0.06 | 3 | 120 | 80 to 110 | 77 | 80 |
| C3 | 0.03 | 3 | 140 | 125 | 100 | 93 |
| C4 | 0.06 | 1.25 | 160 | 140 | 80 | 95 |
| C4 | 0.03 | 3 | 150 | 110 to 140 | 100 | 96 |
| C6 | 0.03 | 0.92 | 200 | 150 | 100 | NC |
| mixture | 0.06 | 1.5 | 180 | 130 | 100 | NC |

The analysis and the yield calculations were performed via analytical techniques known per se, namely by NMR (nuclear magnetic resonance) and by HPLC (high-performance liquid chromatography). The yields are defined relative to the amount of VFA consumed.

The Applicant found that the rate of the reaction, illustrated by decolorization of the reaction mixture after addition of the dibromine, is faster when the amount of anhydride is larger, the purity being little affected. Nevertheless, it is suitable for the temperature for the two steps, the preliminary step and the bromination step, to be optimal.

For this, the Applicant noted that a bromination temperature below the boiling point of the volatile fatty acid is necessary, without being too remote from this temperature.

The various tests made it possible to define that a bromination temperature from about 10° C. to 50° C. below the boiling point of the volatile fatty acid, advantageously 20° C. below, made it possible, all other conditions being identical, to obtain an optimum yield, typically between 60% and 100% with a reaction time of 1 hour to 4 hours.

As regards the role of acetic anhydride, in the light of the results in the table, it appears that the molar percentage of anhydride relative to the VFA must be in the region of 12% for an optimum bromination reaction, it being understood that a percentage of between 5% and 20% is acceptable.

Using the α-bromo acids obtained, or more precisely using a given α-bromo acid, the synthesis is then performed, in step d), of a given α-hydroxylated acid, also called α-hydroxy acid. To do this, a base is added. Advantageously, but not exclusively, it is sodium hydroxide.

Tests were performed by the Applicant by substitution of sodium hydroxide (NaOH) on α-bromo acids, namely on bromoacetic acid, α-bromopropionic acid, α-bromobutyric acid, on α-bromocaproic acid and on a mixture of α-bromo acids containing from two to six carbons. Such a substitution allows the production of α-hydroxy acids bearing a carbon chain of, respectively, two, three, four, five or six carbons, i.e. glycolic acid, lactic acid, α-hydroxybutyric acid, α-hydroxyvaleric acid or α-hydroxycaproic acid.

These α-hydroxy acids are among those most widely used for, after polymerization, producing cosmetics or food packaging. It is readily appreciated that the process that is the subject of the invention allows the production of other types of acids that allow the polymerization of other types of PHA. By way of example, mention may be made of α-hydroxydecanoic acid.

For the various tests, the protocol consisted in bringing to reflux an equimolar mixture of sodium hydroxide and of α-bromo acids for a time of one to two hours. The heating temperature ranges from 80° C. to 120° C. Samples taken at regular intervals made it possible to show that the yield is between 60% and 100% and advantageously between 80% and 100% for the acids containing at least three carbons.

It is also seen that the optimum yield is achieved during gradual increase of the temperature for the compounds containing more than four carbons. The Applicant thus found that the yield is optimal when the temperature remains below a temperature at and above which degradation of the α-hydroxy acid commences, this temperature being de facto less than the boiling point of the α-bromo acid.

In particular, the Applicant has found, surprisingly, that the temperature at which the optimal yield is achieved is between 20° C. and 120° C., advantageously between 50° C. and 90° C.

The Applicant has especially found that, unexpectedly, the temperature at which the optimal yield is achieved is in the region of 50° C. for α-bromo acids containing at least four carbons and in the region of 90° C. for the α-bromo acids containing less than four carbons, it being understood that, for the C2 and C3 α-hydroxy acids, a temperature above 100° C. induces degradation of the compound.

Specifically, once the optimal yield has been reached, extending the reaction time affords only a minimal gain, for example a yield gain of 4% for a reaction time of two hours instead of one hour for an α-bromo acid containing four carbons.

Table 2 below summarizes some of the tests performed.

TABLE 2

| Halo acids | Mol acid | Mol NaOH | Heating temperature (° C.) | Reflux time (h) | Yield (%) |
|---|---|---|---|---|---|
| BrC2 | 0.05 | 0.05 | 110-120 | 2 | 80 |
| BrC2 | 0.05 | 0.05 | 110-120 | 2 | 85 |
| BrC3 | 0.05 | 0.05 | 110-120 | 2 | 80 |
| BrC4 | 0.05 | 0.05 | 110-120 | 2 | 100 |
| BrC4 | 0.05 | 0.05 | 110-120 | 1 | 96 |
| BrC6 + BrC2 | 0.041 + 0.0019 | 0.043 | 100 | 1 | 95 |
| BrC3 + BrC2 | 0.05 + 0.014 | 0.064 | 100 | 2 | 62 |
| BrC2—BrC6 mixture | 0.042 | 0.042 | 80 | 2 | 83 |

The analysis and the yield calculations were performed via the analytical techniques of NMR and HPLC, already mentioned. The yields are defined relative to the initial amount of halo acid.

The final step of the process consists in polymerizing the corresponding polyhydroxyalkanoate or PHA starting with the α-hydroxy acid obtained. By way of example, mention may be made of polylactic acid or PLA, which is used in food packaging, and polyglycolic acid or PGA used in the medical field as suture material. PLA is derived from lactic acid obtained from α-bromopropionic acid. PGA is derived from glycolic acid obtained from bromoacetic acid.

This polymerization, which is known per se, is advantageously performed according to three routes: by ring opening (ring-opening polymerization), by solid-phase polymerization (solid-state polymerization) or by direct polycondensation. This polymerization is followed by recovery of the PHA, which is known per se.

The invention claimed is:

1. A process for producing polyhydroxyalkanoates (PHA), namely homo-, co- or heteropolymer types, by chemical synthesis from volatile fatty acid (VFA) molecules, referred to as precursors, said volatile fatty acid (VFA) molecules being produced by anaerobic fermentation from fermentable biomass, comprising:
   a) extracting the volatile fatty acid (VFA) molecules, without stopping the fermentation and under conditions that are at least non-lethal for all the microorganisms, via an extraction means chosen from liquid or solid extraction means that are, at least, insoluble in the fermentation medium;
   b) collecting, outside the fermentation reactor, the volatile fatty acid (VFA) molecules once they have been extracted;
   c) synthesizing, by chemical synthesis, a given α-halo acid by halogenation, using a volatile fatty acid (VFA) chosen from the volatile fatty acids collected in step b) and said volatile fatty acid (VFA) is defined according to the desired type of PHA and at a temperature below the boiling point of the volatile fatty acid (VFA);
   d) synthesizing from this a-halo acid molecules of a given a-hydroxy acid by reaction with a base; and
   e) polymerizing using the a-hydroxy acid obtained a defined polyhydroxyalkanoate (PHA).

2. The process according to claim 1, wherein, during step c), the halo compound used is dibromine.

3. The process according to claim 1, wherein, during step c), the halo compound used is other than dibromine.

4. The process according to claim 1, wherein, during step c), acetic anhydride is used in a molar percentage relative to the volatile fatty acid in the region of 12%.

5. The process according to claim 1, wherein, during step c), an anhydride corresponding to the volatile fatty acid (VFA) to be halogenated is used.

6. The process according to claim 1, wherein, during step c), the temperature at which the bromination reaction is performed is from 20° C. to 40° C. below the boiling point of the volatile fatty acid.

7. The process according to claim 1, wherein, during step d), the base used is sodium hydroxide.

8. The process according to claim 7, wherein, during step d), the sodium hydroxide is in equimolar amount with the a-halo acid.

9. The process according to claim 7, wherein, during step d), the reaction of the a-halo acid with sodium hydroxide is performed between 20° C. and 120° C., advantageously between 50° C. and 90° C.

10. The process according to claim 9, wherein, during step d), the reaction of the a-halo acid with sodium hydroxide is optimal for a temperature in the region of 50° C. if the a-halo acid contains at least four carbons and for a temperature in the region of 90° C. if the a-halo acid contains less than four carbons.

* * * * *

UNITED STATES PATENT AND TRADEMARK OFFICE
CERTIFICATE OF CORRECTION

| | |
|---|---|
| PATENT NO. | : 9,650,469 B2 |
| APPLICATION NO. | : 15/053666 |
| DATED | : May 16, 2017 |
| INVENTOR(S) | : Nouaille et al. |

It is certified that error appears in the above-identified patent and that said Letters Patent is hereby corrected as shown below:

Claims 1 to 10 should read:

1. A process for producing polyhydroxyalkanoates (PHA), namely homo-, co- or heteropolymer types, by chemical synthesis from volatile fatty acid (VFA) molecules, referred to as precursors, said volatile fatty acid (VFA) molecules being produced by anaerobic fermentation from fermentable biomass, comprising:
a) extracting the volatile fatty acid (VFA) molecules, without stopping the fermentation and under conditions that are at least non-lethal for all the microorganisms, via an extraction means chosen from liquid or solid extraction means that are, at least, insoluble in the fermentation medium;
b) collecting, outside the fermentation reactor, the volatile fatty acid (VFA) molecules once they have been extracted;
c) synthesizing, by chemical synthesis, a given α-halo acid by halogenation, using a volatile fatty acid (VFA) chosen from the volatile fatty acids collected in step b) and said volatile fatty acid (VFA) is defined according to the desired type of PHA and at a temperature below the boiling point of the volatile fatty acid (VFA);
d) synthesizing from this α-halo acid molecules of a given α-hydroxy acid by reaction with a base; and
e) polymerizing using the α-hydroxy acid obtained a defined polyhydroxyalkanoate (PHA).

2. The process according to Claim 1, wherein, during step c), the halo compound used is dibromine.

3. The process according to Claim 1, wherein, during step c), the halo compound used is other than dibromine.

4. The process according to Claim 1, wherein, during step c), acetic anhydride is used in a molar percentage relative to the volatile fatty acid in the region of 12%.

Signed and Sealed this
Third Day of October, 2017

Joseph Matal
*Performing the Functions and Duties of the*
*Under Secretary of Commerce for Intellectual Property and*
*Director of the United States Patent and Trademark Office*

5. The process according to Claim 1, wherein, during step c), an anhydride corresponding to the volatile fatty acid (VFA) to be halogenated is used.

6. The process according to claim 1, wherein, during step c), the temperature at which the bromination reaction is performed is from 20 °C to 40 °C below the boiling point of the volatile fatty acid.

7. The process according to claim 1, wherein, during step d), the base used is sodium hydroxide.

8. The process according to Claim 7, wherein, during step d), the sodium hydroxide is in equimolar amount with the α-halo acid.

9. The process according to Claim 7, wherein, during step d), the reaction of the α-halo acid with sodium hydroxide is performed between 20 °C and 120 °C, advantageously between 50 °C and 90 °C.

10. The process according to Claim 9, wherein, during step d), the reaction of the α-halo acid with sodium hydroxide is optimal for a temperature in the region of 50 °C if the α-halo acid contains at least four carbons and for a temperature in the region of 90 °C if the α-halo acid contains less than four carbons.